United States Patent [19]

Ávár et al.

[11] 4,102,857
[45] Jul. 25, 1978

[54] PYRAZOLE DERIVATIVES

[75] Inventors: Lajos Ávár, Biel-Benken; Kurt Hofer, Munchenstein; Martin Preiswerk, Basel, all of Switzerland

[73] Assignee: Sandoz Ltd., Basel, Switzerland

[21] Appl. No.: 716,345

[22] Filed: Aug. 20, 1976

Related U.S. Application Data

[63] Continuation-in-part of Ser. No. 486,345, Jul. 8, 1974, Pat. No. 3,976,658.

[30] Foreign Application Priority Data

Jul. 13, 1973 [CH] Switzerland ............... 10248/73

[51] Int. Cl.$^2$ ............................................. C08K 5/34
[52] U.S. Cl. .......................... 260/45.8 N; 106/163 R; 260/45.8 A; 260/45.8 NZ; 260/45.8 RW; 260/45.8 SN; 260/800; 260/880 R; 548/377
[58] Field of Search ............. 260/45.8 N, 310 R; 252/301.27; 548/377

[56] References Cited

U.S. PATENT DOCUMENTS

| T887,007 | 6/1971 | Dallon et al. ............... 96/100 R |
| 2,476,986 | 7/1949 | Martin ........................ 260/310 R |
| 2,946,765 | 7/1960 | Roos et al. ................. 260/45.8 N |
| 3,205,083 | 9/1965 | Green ......................... 260/45.8 N |
| 3,215,550 | 11/1965 | Strobel et al. ............ 260/45.8 N |
| 4,002,641 | 1/1977 | Moller et al. ................ 548/363 |
| 4,008,200 | 2/1977 | Avar et al. ................ 260/45.8 N |

OTHER PUBLICATIONS

Huston et al. J.A.C.S., vol. 55, 1933, pp. 3407 and 3408.

*Primary Examiner*—Melvyn I. Marquis
*Assistant Examiner*—R. A. White
*Attorney, Agent, or Firm*—Gerald D. Sharkin; Richard E. Vila; Joseph J. Borovian

[57] ABSTRACT

New ultraviolet light-absorbing compounds of the formula

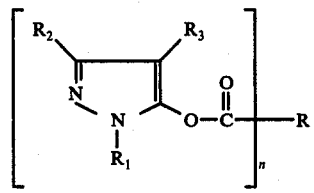

in which
$R_1$ is a substituent, e.g. alkyl,
$R_2$ is a substituent, e.g. alkyl,
$R_3$ is hydrogen or a substituent, e.g. alkyl,
n is 1, 2 or 3, and
R is an n-valent, optionally substituted benzene radical, or a 1- or 2-valent naphthalene or heterocyclic radical, which are producible by known processes. Such compounds are useful as stabilizers of organic materials, particularly plastics materials, against the degrading action of ultraviolet light and can be either applied as a coating on the organic material, or incorporated therein.

Such compounds are useful as stabilizers of organic materials, particularly plastics materials, against the degrading action of ultraviolet light and can be either applied as a coating on the organic material, or incorporated therein.

16 Claims, No Drawings

PYRAZOLE DERIVATIVES

This application is a continuation-in-part of copending application Ser. No. 486,345, filed July 8, 1974, which issued as U.S. Pat No. 3,976,658 on Aug. 24, 1976.

The present invention relates to a class of novel pyrazole derivatives which are useful as stabilizers of organic materials against the adverse effects of ultraviolet light.

Accordingly, the present invention provides a class of compounds of the formula I,

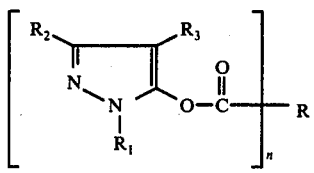

in which
  $R_1$ is a $C_{1-22}$ alkyl radical, a $C_{5-12}$ cycloalkyl radical, a $C_{6-12}$ cycloalkyl-alkyl radical, a $C_{7-12}$ aralkyl radical, of which the alkyl radical and the alkyl moiety of the cycloalkylalkyl radical are uninterrupted or interrupted by 1 or 2 sulphur atoms or by -COO-, and the aryl nucleus of the aralkyl radical is unsubstituted or substituted by a hydroxyl group and/or 1 or 2 $C_{1-12}$ alkyl radicals, or a phenyl group, unsubstituted or substituted by one or more substituents selected from 1 or 2 halogen atoms, a cyano group, a hydroxyl group, 1 or 2 $C_{1-12}$ alkyl radicals, 1 or 2 $C_{1-12}$ alkoxy radicals, a phenyl group and the radicals $R_4$—O— and $R_4$—$SO_2$—, wherein $R_4$ is a phenyl group, unsubstituted or substituted by 1 or 2 $C_{1-8}$ alkyl radicals,
  $R_2$, independently of $R_1$, has one of the significances of $R_1$, or is a cyano group or the radical —$COOR_5$, wherein $R_5$ is a $C_{1-12}$ alkyl radical, a $C_{5-12}$ cycloalkyl radical, a $C_{6-12}$ cycloalkyl-alkyl radical or a phenyl group, unsubstituted or substituted by a hydroxyl group and/or 1 or 2 $C_{1-8}$ alkyl radicals,
  $R_3$ is a hydrogen atom or one of the significances of $R_1$, —$COR_1$ or —$COOR_5$, $n$ is 1, 2 or 3,
  and R, when $n$ is 1, is a phenyl group, unsubstituted or substituted by a total of up to 3 substituents selected from 1 hydroxyl group, 1 to 3 halogen atoms, 1 phenyl group, 1 benzyl group, 1 phenoxy group, 1 to 3 alkyl radicals each containing 1 to 8 carbon atoms and the sum of the carbon atoms not exceeding 12, and 1 to 3 alkoxy radicals each containing 1 to 22 carbon atoms and the sum of the carbon atoms not exceeding 22, or a monovalent napthalene radical, or a monovalent radical of thiophene, benzothiophene, dibenzothiophene, furan, benzofuran or dibenzofuran, and when $n$ is 2, is a phenylene group, unsubstituted or substituted by a $C_{1-4}$ alkyl radical and/or a halogen atom, or a divalent naphthalene radical, or a divalent radical of thiophene or dibenzofuran, and when $n$ is 3, is a 1,3,5-trivalent benzene radical.

A preferred group of ultraviolet stabilizing compounds of the formula I are those of the formula I$a$,

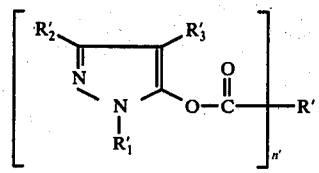

in which each of
  $R_1'$ and $R_1''$, independently, is a $C_{1-8}$ alkyl radical or a phenyl group, unsubstituted or substituted by up to 4 substituents selected from a hydroxyl group, a halogen atom and 1 or 2 $C_{1-4}$ alkyl radicals,
  $R_3'$ is a hydrogen atom or one of the significances of $R_1'$ or -$COR_1'$,
  $n'$ is 1 or 2,
  and R', when $n$ is 1, is a phenyl group, unsubstituted or substituted by a total of up to 3 substituents selected from 1 hydroxyl group, 1 $C_{1-6}$ alkoxy radical and 1 to 3 $C_{1-6}$ alkyl radicals, the sum of the carbon atoms of these substituents not exceeding 12, and when $n$ is 2, is a phenylene group, unsubstituted or substituted by a $C_{1-4}$ alkyl radical;

A preferred group of ultraviolet stabilizing compounds of the formula I$a$ are those of the formula I$b$,

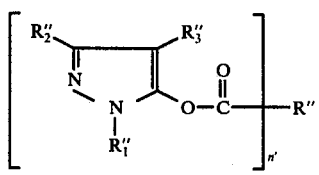

in which each of
  $R_1''$ and $R_2'''$, independently, is a $C_{1-4}$ alkyl radical or a phenyl group, unsubstituted or substituted by a halogen atom,
  $R_3''$ is a hydrogen atom or one of the significances of $R_1'$, as hereinbefore defined,
  $n'$ is 1 or 2,
  and R'', when $n$ is 1, is a phenyl group, unsubstituted or substituted by a total of up to 3 substituents selected from 1 hydroxyl group, 1 $C_{1-4}$ alkoxy radical and 1 to 3 $C_{1-4}$ alkyl radicals, the sum of the carbon atoms of these substituents not exceeding 10, and when $n$ is 2, is a phenylene group;

A preferred group of ultraviolet stabilizing compounds of the formula I$b$ are those of the formula I$c$

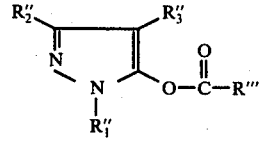

in which
  $R_1''$, $R_2''$ and $R_3''$ are as previously defined,
  and R''' is a phenyl group which is substituted in the ortho- or paraposition by a hydroxyl group and by 1 or 2 tertiary butyl groups in meta-position(s) adjacent to the hydroxyl group, or by a $C_{1-4}$ alkoxy radical.

In this specification, an alkyl radical, if not otherwise stated, may be primary, secondary or tertiary, and may be derived from a natural aliphatic hydrocarbon which is branched in any way. Examples of primary alkyl radicals are methyl, ethyl, n-propyl, n-butyl, n-pentyl, n-hexyl and unbranched primary $C_{7-22}$ alkyl radicals, of secondary alkyl radicals are isopropyl and 2-butyl, and of tertiary alkyl radicals are tertiary butyl and 2-methyl-2-butyl. Examples of alkyl radicals with the appropriate number of carbon atoms serve to exemplify the alkyl moieties of alkoxy radicals.

Examples of cycloalkyl radicals are cyclopentyl, cyclohexyl, cycloheptyl and cyclododecyl, and of cycloalkyl-alkyl are cyclohexyl-methyl and 2-cyclohexyl-ethyl. To exemplify aralkyl radicals envisaged in this specification may be mentioned benzyl and 2-phenylethyl.

By the term 'halogen' is meant fluorine, chlorine or bromine, of which chlorine is the preferred halogen atom.

Alkyl radicals or cycloalkyl-alkyl radicals whose aliphatic chains are interrupted by 1 or 2 sulphur atoms or by -COO- are exemplified by $CH_3-S-CH_2CH_2-$, $C_{12}H_{25}-S-(CH_2)_8-$, $C_2H_5OCOCH_2-$, $C_{12}H_{25}OCOCH_2-$ and $C_8H_{17}OCOCH_2-$.

Examples of $R_1$ when signifying a substituted phenyl group are

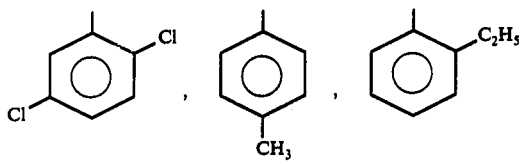

and

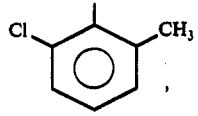

and examples of R are

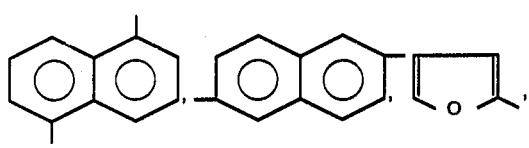

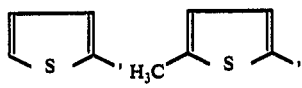

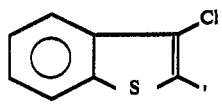

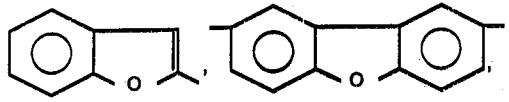

-continued

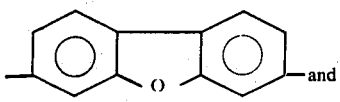 and

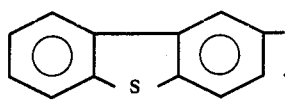

In the above formulae I, Ia and Ib, n or n' is preferably 1 and the preferred meaning of R, R' and R", respectively, is a phenyl group which is substituted in the ortho- or para-position by a hydroxyl group and by 1 or 2 tertiary butyl groups in meta-position(s) adjacent to the hydroxyl group, or by a $C_{1-4}$ alkoxy radical.

The present invention also provides a process for producing a compound of the formula I, which comprises reacting a compound of the formula II,

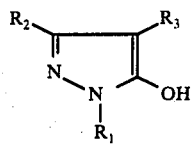 II in which $R_1$, $R_2$ and $R_3$ are as defined above, with a compound of the formula III, R — (COOH)$_n$     III in which R and n are as defined above, or a functional derivative thereof.

The reaction between the compounds of the formulae II and III is advantageously effected in a reaction-inert organic solvent, in which the reagents may be dissolved or even suspended, preferably by heating within the temperature range 20° C to 110° C. Suitable solvents for the reaction include benzene, xylene, cymene, diphenylether, tetrahydrofuran and dioxan.

When an acid chloride is used as the functional derivative of a compound of the formula III, this being the preferred functional derivative, hydrogen chloride is liberated in the reaction. In such a case, an acid-binding agent, e.g. lime, an alkali metal carbonate or bicarbonate, pyridine, a trialkylamine or a dialkylaniline, is preferably present in the reaction medium. Additionally it is preferable to effect the reaction in the absence of humidity.

The present invention further provides a method of stabilizing an organic material against the action of ultraviolet light comprising treating the organic material with a compound of the formula I, as hereinbefore defined. By the term "treating" as used herein, is meant either incorporating into the body of the organic material, or surface coating the organic material, in a manner known per se. Thus the method of the invention comprises treating the organic material, either by way of mixing the compound of the formula I with the organic material, or by way of coating the compound of the formula I as a protective layer on the surface of the organic material. Through its ultraviolet light-absorbing property, the compound of the formula I, incorporated in or coated on an organic material sensitive to ultraviolet light, protects the material from the degradative action of ultraviolet light.

Suitable organic materials for such protective treatment include polyolefins, especially polyethylene and polypropylene, polyesters, polymethylmethacrylates, polyphenylene oxides, polyurethanes, polystyrene, ABS-terpolymers, polyamides, especially nylon, polypropylene oxide, polyacrylonitrile and copolymers of the aforementioned polymers. Preferably the compounds of the formula I are used, according to the method of the present invention, to stabilize polypropylene, polyethylene, polyester, polyamide, polyurethane, polyacrylonitrile, ABS-terpolymers, terpolymers of acrylic ester, styrene and acrylonitrile, and copolymers of styrene and acrylonitrile and of styrene and butadiene. As well as the aforementioned synthetic materials, natural materials, e.g. rubber, cellulose, wool and silk, may be stabilized by a compound of the formula I according to the method of the present invention.

The materials to be protected according to the method of the present invention may be in the form of plates, rods, coatings, sheets, fibres, strips, films, granules, powders and other solid forms, or in solutions, emulsions or dispersions.

The incorporation into or coating of the particular organic material to be treated with a compound of the formula I may be effected by known methods. In one embodiment of the method of the invention, the organic material, for example in granular form, is intimately mixed with one or more compounds of the formula I, for example in a kneader or other suitable mixing device, and is subsequently extruded to its final form. Examples of the forms taken by the product of such a process are sheets, loops and filaments. In another embodiment, textile threads or fabrics are treated with one or more compounds of the formula I in an aqueous bath containing the stabilizer in dispersion. Textiles of polyethylene terephthalate an cellulose acetate are particularly suitable for such processing.

Synthetic materials do not necessarily have to be completely polymerised or condensed before treatment with compounds of the formula I, since monomers of prepolymers may be mixed with such stabilisers and thereafter converted to products in their final forms by condensation or polymerisation.

The compounds of the present invention are not only employable for the stabilization against ultraviolet light of clear films, but may also be used to stabilize opaque, semi-opaque or translucent organic materials whose surfaces are susceptible to degradation by ultraviolet light. Examples of such latter materials are foamed plastics, opaque films and coatings, opaque papers, transparent and opaque dyed plastics, fluorescent pigments, automobile and furniture polishes, creams and lotions.

The amount of stabilizer of the formula I suitably employed in the method of the present invention will naturally depend on the mode of application, the particular compound of formula I employed, and the nature and form of the organic material to be treated. However, in general satisfactory results are obtained when the amount of stabilizer of the formula I employed is between 0.01 and 5%, preferably between 0.05 and 1%, of the weight of the organic material to be treated.

The stabilized organic material may only contain, as ultraviolet stabilizer, one or more compounds of the formula I, or it may additionally contain other adjuvants for improving its properties. Such other adjuvants may be, for example, further stabilizers or co-stabilizers against the adverse effects of heat, oxygen or ultraviolet light, and they may belong to quite different chemical classes to that of the compounds of formula I.

A further feature of the present invention comprises the organic materials which contain one or more compounds of the formula I as stabilizers against the adverse effects of ultraviolet light. In accordance with the methods hereinbefore described for the production of such stabilized organic materials, the latter may contain from 0.01 to 5% by weight of one or more compounds of the formula I as stabilizing agent, or preferably from 0.05 to 1% by weight.

In the following Examples, which illustrates the compounds of the present invention, processes for their production and methods of their application, the parts and percentages are by weight and the temperatures are in degrees centigrade. The indicated structures are verified by microanalysis and spectroscopic analysis.

EXAMPLE 1

23.6 Parts of 1,3-diphenyl-pyrazol-5-one and 8 parts of pyridine are added to 200 parts of toluene. 26.8 Parts of 3,5-di-tert.-butyl-4-hydroxybenzoyl chloride are added in portions to the solution whilst stirring, at 20° C, and the solution is left to react further at this temperature until no pyrazolone is detectable. The mixture is then washed with water, the organic phase is separated and dried, and the solvent distilled off. The residue is crystallized from ethanol. The compound having a melting point of 150° to 151° C of formula

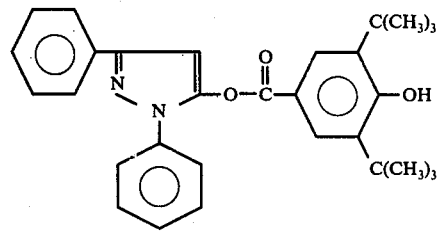

is obtained.

EXAMPLE 2

11.8 Parts of 1,3-diphenyl-pyrazol-5-one and 6.0 parts of triethylamine are added to 100 parts of toluene. 9.8 Parts of 4-tert.-butyl-benzoyl chloride are added in portions to the solutions whilst stirring, at 60° C, and the solution is left to react further at this temperature until no pyrazolone is detectable. The mixture is then washed with water, the organic phase is separated, dried and the solvent distilled off. The residue is crystallized from hexane. The compound having a melting point of 160° to 107° C of formula

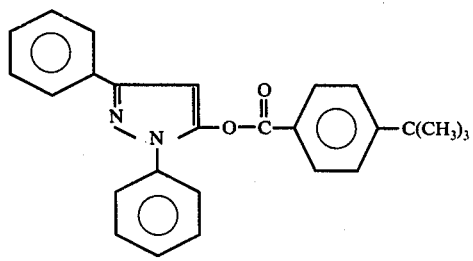

is obtained.

The following compounds, which are listed in Table 1, are produced in a similar manner.

TABLE I $$\underset{\underset{R_1}{|}}{\overset{R_2}{\underset{N}{\diagdown}}\underset{N}{\diagup}}\overset{R_3}{\underset{O-\overset{O}{\overset{\|}{C}}-R}{\diagdown}}$$

| No. | $R_1$ | $R_2$ | $R_3$ | R | M.p. |
|---|---|---|---|---|---|
| 1 | phenyl | $CH_3-$ | 3-hydroxy-4-(di-t-butyl)benzoyl | 3,5-di-t-butyl-4-hydroxyphenyl | 215-216° C |
| 2 | phenyl | $CH_3-$ | 4-t-butylbenzoyl | 3,5-di-t-butyl-4-hydroxyphenyl | 170-172° C |
| 3 | $CH_3-$ | $CH_3-$ | H | 3,5-di-t-butyl-4-hydroxyphenyl | 139-140° C |
| 4 | phenyl | $CH_3-$ | H | 3,5-di-t-butyl-4-hydroxyphenyl | 152-154° C |
| 5 | phenyl | $C_3H_7-$ | H | 3,5-di-t-butyl-4-hydroxyphenyl | 93-95° C |
| 6 | 4-methylphenyl | $CH_3-$ | H | 3,5-di-t-butyl-4-hydroxyphenyl | 140-141 |
| 7 | phenyl | $CH_3-$ | H | 2-methoxy-3,5-di-t-butylphenyl | 81-82 |
| 8 | 3-chlorophenyl | $CH_3-$ | H | 3,5-di-t-butyl-4-hydroxyphenyl | 132-133 |
| 9 | 4-chlorophenyl | $CH_3-$ | H | 3,5-di-t-butyl-4-hydroxyphenyl | 86-88 |
| 10 | 2-chlorophenyl | $CH_3-$ | H | 3,5-di-t-butyl-4-hydroxyphenyl | 130-131 |
| 11 | phenyl | $CH_3-$ | $C_2H_5-$ | 3,5-di-t-butyl-4-hydroxyphenyl | 144-145 |
| 12 | phenyl | $CH_3-$ | $-C_4H_9(n)$ | 3,5-di-t-butyl-4-hydroxyphenyl | 134-135 |
| 13 | phenyl | $-COOC_2H_5$ | H | 3,5-di-t-butyl-4-hydroxyphenyl | 63-64 |
| 14 | phenyl | phenyl | H | 4-methoxyphenyl | 135-136 |

TABLE I-continued

| No. | $R_1$ | $R_2$ | $R_3$ | R | M.p. |
|---|---|---|---|---|---|
| 15 | phenyl | phenyl | H | 3,5-di-t-butyl-4-hydroxyphenyl | 120–121 |

+ signifies —C(CH$_3$)$_3$

In a similar manner, the following compounds were also produced

No. 16

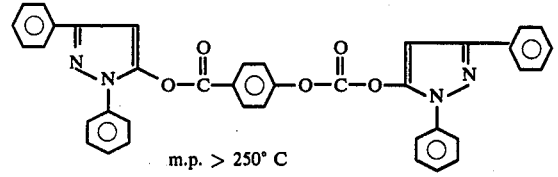

m.p. > 250° C

No. 17

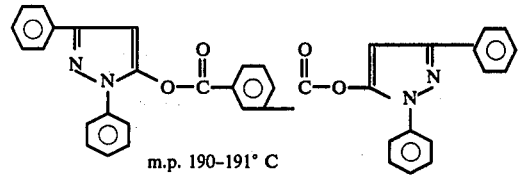

m.p. 190–191° C

EXAMPLE 3

To a solution of 31.6 g of pyridine and 22.4 g of 1,3-dimethyl pyrazolone in 200 g of toluene are added within the temperature range 65°–69° C and with stirring 41.9 g of 2,4-dichlorobenzoyl chloride over a period of 45 minutes. After one hours reaction, 100 g of water are added to the mixture.

The organic layer is separated, washed with water and the solvent removed by distillation. Recrystallization of the residual reaction product from ethanol yields white crystals m.p. 95°–97° C. The product has the formula:

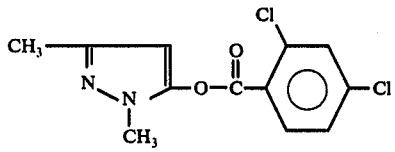

Analysis: Calc. C 50.5%; H 3.5%; N 9.8%; Cl 24.9%. Found 50.8%; 3.7%; 9.6%; 24.7%.

APPLICATION EXAMPLE

Non-stabilized polypropylene is mixed intimately with 0.5% of the compound of Examples 1, 2 and Nos. 1, 6 and 7 of Table 1 on a roller mill at 180° C and is processed to form sheets of 0.3 mm thickness. These are tested in the climate test to demonstrate their resistance against the action of ultraviolet light by the De La Rue method. The test is carried out at 40° C, with 75% relative humidity and strong ventilation, using 16 Philips Sunlamps and 16 Philips Blacklamps. Stabilized polypropylene shows considerably better results than nonstabilized polypropylene. Non-stabilized polyvinyl chloride and polyvinyl chloride containing 0.5% of the compound No. 1 of Table 1 are tested similarly in the climate test.

Similar results may be obtained for polyethylene, ABS-terpolymers, polyethylene terephthalate, cellulose acetobutyrate, polyamide 6, polystyrene, polycarbonate and polyurethane.

What is claimed is:

1. A compound of the formula,

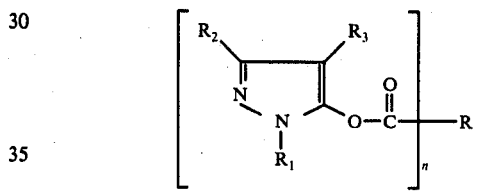

wherein $R_1$ is $C_{1-22}$ alkyl, uninterrupted or interrupted by 1 or 2 sulfur atoms or by —COO—; $C_{5-12}$ cycloalkyl; $C_{6-12}$ cycloalkyl-alkyl, of which the alkyl moiety is uninterrupted or interrupted by 1 or 2 sulfur atoms or by —COO—; $C_{7-12}$ aralkyl, of which the aryl nucleus is unsubstituted, monosubstituted by hydroxy, monosubstituted by $C_{1-12}$ alkyl, disubstituted by $C_{1-12}$ alkyl, monosubstituted by hydroxy and monosubstituted by $C_{1-12}$ alkyl, or monosubstituted by hydroxy and disubstituted by $C_{1-12}$ alkyl; unsubstituted phenyl; or phenyl substituted by one or more substituents independently selected from halo, cyano, hydroxy, $C_{1-12}$ alkyl, $C_{1-12}$ alkoxy, unsubstituted phenyl, $R_4$—O— and $R_4$—SO$_2$—, wherein $R_4$ is unsubstituted phenyl, phenyl monosubstituted by $C_{1-8}$ alkyl or phenyl disubstituted by $C_{1-8}$ alkyl, with the proviso that the maximum number of each substituent selected from cyano, hydroxy, unsubstituted phenyl, $R_4$—O— and $R_4$—SO$_2$— is one and the maximum number of each substitutent selected from halo, $C_{1-12}$ alkyl and $C_{1-12}$ alkoxy is two;

$R_2$ is cyano; —COOR$_5$, wherein $R_5$ is $C_{1-12}$ alkyl, $C_{5-12}$ cycloalkyl, $C_{6-12}$ cycloalkyl-alkyl, unsubstituted phenyl, phenyl monosubstituted by hydroxy, phenyl monosubstituted by $C_{1-8}$ alkyl, phenyl disubstituted by $C_{1-8}$ alkyl, phenyl monosubstituted by hydroxy and monosubstituted by $C_{1-8}$ alkyl, or phenyl monosubstituted by hydroxy and disubstituted by $C_{1-8}$ alkyl; or one of the significances of $R_1$;

$R_3$ is hydrogen; —$COR_1$; —$COOR_5$; or one of the significances of $R_1$;

n is 2 or 3; and

R, when n is 2, is unsubstituted phenylene; phenylene monosubstituted by $C_{1-4}$ alkyl; phenylene monosubstituted by halo; phenylene monosubstituted by $C_{1-4}$ alkyl and monosubstituted by halo; divalent naphthalene; divalent thiophene; or divalent dibenzofuran; and when n is 3 is 1,3,5-trivalent benzene.

2. A compound of the formula,

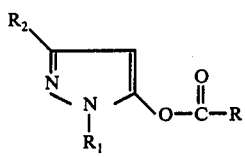

wherein each of $R_1$ and $R_2$ is, independently, $C_{1-4}$ alkyl or unsubstituted phenyl; and R is phenyl substituted by 1 to 3 substituents independently selected from hydroxy, halo, unsubstituted phenyl, unsubstituted benzyl, unsubstituted phenoxy, $C_{1-8}$ alkyl and $C_{1-22}$ alkoxy; with the provisios that: a) the maximum number of each substituent selected from hydroxy, unsubstituted phenyl, unsubstituted benzyl and unsubstituted phenoxy is one; b) when phenyl is di- or trisubstituted by $C_{1-8}$ alkyl, the sum of the carbon atoms of the alkyl substitutents does not exceed 12; c) when phenyl is di- or trisubstituted by $C_{1-22}$ alkoxy, the sum of the carbon atoms of the alkoxy substitutents does not exceed 22; and d) R is other than phenyl monosubstituted in the ortho- or para-position by a hydroxy group and mono- or disubstituted in the meta-position(s) by a tertiary butyl group, wherein the tertiary butyl group or at least one of the two tertiary butyl groups is adjacent to the hydroxy group; or phenyl monosubstituted by $C_{1-4}$ alkoxy.

3. A method of stabilizing an organic natural or synthetic polymeric material susceptible to degradation under the effect of ultraviolet light which comprises treating said material with a stabilizing effective amount of a compound of the formula,

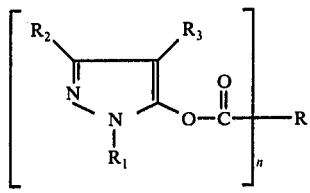

wherein $R_1$ is $C_{1-22}$ alkyl, uninterrupted or interrupted by 1 or 2 sulfur atoms or by —COO—; $C_{5-12}$ cycloalkyl; $C_{6-12}$ cycloalkyl-alkyl, of which the alkyl moiety is uninterrupted or interrupted by 1 or 2 sulfur atoms or by —COO—; $C_{7-12}$ aralkyl, of which the aryl nucleus is unsubstituted, monosubstituted by hydroxy, monosubstituted by $C_{1-12}$ alkyl, disubstituted by $C_{1-12}$ alkyl, monosubstituted by hydroxy and monosubstituted by $C_{1-12}$ alkyl, or monosubstituted by hydroxy and disubstituted by $C_{1-12}$ alkyl; unsubstituted phenyl; or phenyl substituted by one or more substituents independently selected from halo, cyano, hydroxy, $C_{1-12}$ alkyl, $C_{1-12}$ alkoxy, unsubstituted phenyl, $R_4$—O— and $R_4$—$SO_2$—, wherein $R_4$ is unsubstituted phenyl, phenyl monosubstituted by $C_{1-8}$ alkyl or phenyl disubstituted by $C_{1-8}$ alkyl, with the proviso that the maximum number of each substituent selected from cyano, hydroxy, unsubstituted phenyl, $R_4$—O— and $R_4$—$SO_2$— is one and the maximum number of each substituent selected from halo, $C_{1-12}$ alkyl and $C_{1-12}$ alkoxy is two;

$R_2$ is cyano; —$COOR_5$, wherein $R_5$ is $C_{1-12}$ alkyl, $C_{5-12}$ cycloalkyl, $C_{6-12}$ cycloalkyl-alkyl, unsubstituted phenyl, phenyl monosubstituted by hydroxy, phenyl monosubstituted by $C_{1-8}$ alkyl, phenyl disubstituted by $C_{1-8}$ alkyl, phenyl monosubstituted by hydroxy and monosubstituted by $C_{1-8}$ alkyl, or phenyl monosubstituted by hydroxy and disubstituted by $C_{1-8}$ alkyl; or one of the significances of $R_1$;

$R_3$ is hydrogen; —$COR_1$; —$COOR_5$; or one of the significances of $R_1$;

n is 1, 2 or 3; and

R, when n is 1, is unsubstituted phenyl; phenyl substituted by 1 to 3 substitutents independently selected from hydroxy, halo, unsubstituted phenyl, unsubstituted benzyl, unsubstituted phenoxy, $C_{1-8}$ alkyl and $C_{1-22}$ alkoxy, with the provisos that: a) the maximum number of each substitutent selected from hydroxy, unsubstituted phenyl, unsubstituted benzyl and unsubstituted phenoxy is one; b) when phenyl is di- or trisubstituted by $C_{1-8}$ alkyl, the sum of the carbon atoms of the alkyl substitutents does not exceed 12; and c) when phenyl is di- or trisubstituted by $C_{1-22}$ alkoxy, the sum of the carbon atoms of the alkoxy substitutents does not exceed 22; monovalent naphthalene; monovalent thiophene; monovalent benzothiophene; monovalent dibenzothiophene; monovalent furan; monovalent benzofuran; or monovalent dibenzofuran; and when n is 2, is unsubstituted phenylene; phenylene monosubstituted by $C_{1-4}$ alkyl; phenylene monosubstituted by halo; phenylene monosubstituted by $C_{1-4}$ alkyl and monosubstituted by halo; divalent naphthalene; divalent thiophene; or divalent dibenzofuran; and when n is 3, is 1,3,5-trivalent benzene.

4. A method according to claim 3, in which the compound is of the formula,

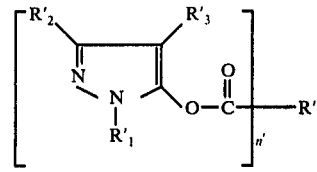

wherein each of $R'_1$ and $R'_2$, independently, is $C_{1-8}$ alkyl; unsubstituted phenyl; or phenyl substituted by 1 to 4 substitutents independently selected from hydroxy, halo and $C_{1-4}$ alkyl, with the proviso that not more than one substitutent is hydroxy, not more than one substitutent is halo and not more than two substitutents are $C_{1-4}$ alkyl;

$R'_3$ is hydrogen; —$COR'_1$; or one of the significances of $R'_1$;

n' is 1 or 2; and

R', when n' is 1, is unsubstituted phenyl; or phenyl substituted by 1 to 3 substituents independently selected from hydroxy, $C_{1-6}$ alkoxy and $C_{1-6}$ alkyl, with the proviso that the maximum number of each substitutent selected from hydroxy and $C_{1-6}$ alkoxy is one, and with the further proviso that when phenyl is trisubstituted by $C_{1-6}$ alkyl, the sum of the carbon atoms of the alkyl substituents does not exceed 12; and when n' is 2, is unsubstituted phenylene or phenylene monosubstituted by $C_{1-4}$ alkyl.

5. A method according to claim 4, in which the compound is of the formula,

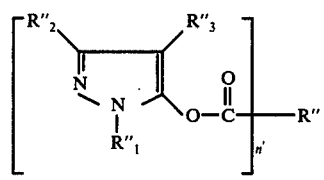

wherein each of
$R''_1$ and $R''_2$, independently, is $C_{1-4}$ alkyl; unsubstituted phenyl; or phenyl monosubstituted by halo;
$R''_3$ is hydrogen; or one of the significances of $R'_1$, as defined in claim 4;
n' is 1 or 2; and
R'', when n' is 1, is unsubstituted phenyl; or phenyl substituted by 1 to 3 substitutents indenpendently selected from hydroxy, $C_{1-4}$ alkoxy and $C_{1-4}$ alkyl, with the proviso that the maximum number of each substituent selected from hydroxy and $C_{1-4}$ alkoxy is one, and with the further proviso that when phenyl is trisubstituted by $C_{1-4}$ alkyl, the sum of the carbon atoms of the alkyl substituents does not exceed 10; and when n' is 2, is unsubstituted phenylene.

6. A method according to claim 3, in which the compound is one wherein n is 1; $R_1$ and $R_2$, independently, are $C_{1-4}$ alkyl or unsubstituted phenyl; $R_3$ is hydrogen; and R is phenyl substituted by 1 to 3 substitutents independently selected from hydroxy, halo, unsubstituted phenyl, unsubstituted benzyl, unsubstituted phenoxy, $C_{1-8}$ alkyl and $C_{1-22}$ alkoxy, with the provisos that: a) the maximum number of each substitutent selected from hydroxy, unsubstituted phenyl, unsubstituted benzyl and unsubstituted phenoxy is one; b) when phenyl is di- or trisubstituted by $C_{1-8}$ alkyl, the sum of the carbon atoms of the alkyl substitutents does not exceed 12; and c) when phenyl is di- or trisubstituted by $C_{1-22}$ alkoxy, the sum of the carbon atoms of the alkoxy substituents does not exceed 22.

7. A method according to claim 5, in which the compound is one wherein R'' is phenyl monosubstituted in the ortho- or paraposition by a hydroxy group and mono- or disubstituted in the metaposition(s) by a tertiary butyl group, wherein the tertiary butyl group or at least one of the two tertiary butyl groups is adjacent to the hydroxy group; or phenyl monosubstituted by $C_{1-4}$ alkoxy.

8. A method according to claim 3, in which the natural or synthetic polymeric material is selected from polyolefins, polyesters, polymethylmethacrylates, polyphenylene oxides, polyurethanes, polystyrene, polyamides, polypropylene oxide, polyacrylonitrile, copolymers of styrene and acrylonitrile and of styrene and butadiene, acrylonitrile-butadiene-styrene-terpolymers, terpolymers of acrylic ester, styrene and acrylonitrile, rubber cellulose, wool and silk.

9. A method according to claim 3, in which the compound is one in which n is 1; and, simultaneously, $R_1$ and $R_2$, independently, are other than $C_{1-4}$ alkyl or unsubstituted phenyl; $R_3$ is other than hydrogen; and R is other than phenyl, monosubstituted in the ortho- or para-position by a hydroxy group and mono- or disubstituted in the meta-position(s) by a tertiary butyl group, wherein the tertiary butyl group or at least one of the two tertiary butyl groups is adjacent to the hydroxy group; or phenyl monosubstituted by $C_{1-4}$ alkoxy.

10. A method according to claim 7, in which the compound is one of formula,

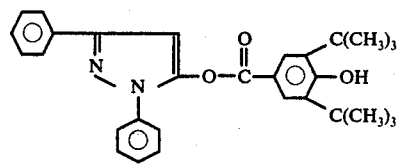

11. A method according to claim 5, in which the compound is one of formula,

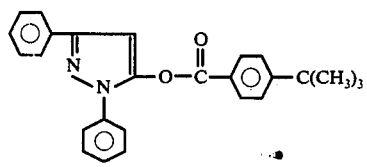

12. A method according to claim 7, in which the compound is one of formula,

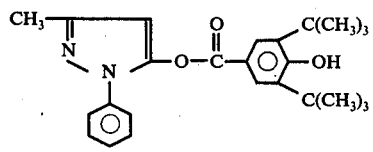

13. A method according to claim 7, in which the compound is one of formula,

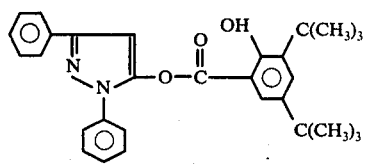

14. A method according to claim 7, in which the compound is one of formula,

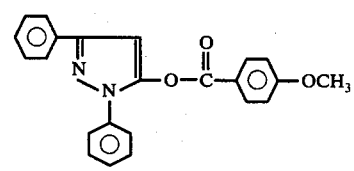

15. A method according to claim 3, in which the stabilizing compound is employed in an amount between 0.01 and 5% by weight of the natural or synthetic polymeric material to be treated.

16. A method according to claim 13, in which n is 2 or 3.

* * * * *